(12) United States Patent
Doran

(10) Patent No.: US 6,179,799 B1
(45) Date of Patent: Jan. 30, 2001

(54) ORTHOSIS FOR SUPINATION AND PRONATION OF THE WRIST

(76) Inventor: Robert E. Doran, 1000 N. State St. #301, Hemet, CA (US) 92543

( * ) Notice: Under 35 U.S.C. 154(b), the term of this patent shall be extended for 0 days.

(21) Appl. No.: 09/241,155

(22) Filed: Feb. 1, 1999

(51) Int. Cl.[7] .................................................. A61F 5/00
(52) U.S. Cl. ................................ 602/20; 602/5; 602/16; 602/21
(58) Field of Search .................................... 602/5, 16, 20, 602/21, 60, 61, 62, 64; 482/45, 907; 601/33, 40

(56) References Cited

U.S. PATENT DOCUMENTS

| 2,312,523 | 3/1943 | Corbett . | |
| 2,357,323 | 9/1944 | Goldberg . | |
| 2,542,316 | 2/1951 | Farrar, Jr. ................................... | 3/12 |
| 2,626,398 | 1/1953 | Grindle et al. ........................... | 3/12.2 |
| 2,767,708 | 10/1956 | Keropian . | |
| 3,089,700 | 5/1963 | Hotas ...................................... | 272/80 |
| 3,631,542 | 1/1972 | Potter ...................................... | 3/1.1 |
| 3,683,897 | 8/1972 | Shield et al. . | |
| 3,707,963 | 1/1973 | Keropian . | |
| 4,237,873 | 12/1980 | Terry et al. . | |
| 4,258,441 | 3/1981 | Bell ......................................... | 3/12.6 |
| 4,433,679 | 2/1984 | Mauldin et al. . | |
| 4,538,595 | 9/1985 | Hajianpour . | |
| 4,559,932 | 12/1985 | Salort . | |
| 4,809,688 | 3/1989 | Aymerica del Valle et al. . | |
| 5,002,044 | 3/1991 | Carter . | |
| 5,103,807 | 4/1992 | Makaran . | |
| 5,117,814 | 6/1992 | Luttrell et al. . | |
| 5,219,323 | 6/1993 | Singer et al. ............................ | 602/16 |
| 5,254,078 | 10/1993 | Carter et al. ............................ | 602/21 |
| 5,279,545 | 1/1994 | Reese, Sr. ................................ | 602/21 |
| 5,484,394 | 1/1996 | Singer et al. ............................ | 602/16 |
| 5,662,594 | 9/1997 | Rosenblatt .............................. | 602/16 |
| 5,662,595 | 9/1997 | Chesher et al. ......................... | 602/20 |
| 5,681,269 | 10/1997 | Basaj et al. .............................. | 602/22 |
| 5,683,353 | 11/1997 | Hamersly ................................ | 602/16 |
| 5,685,830 | 11/1997 | Bonutti ................................... | 602/16 |
| 5,759,165 | * 6/1998 | Malewicz ................................ | 602/21 |
| 5,778,449 | 7/1998 | Oetting et al. ........................... | 2/16 |

OTHER PUBLICATIONS

North Coast Medical 1998 Hand Therapy Catalog p. 87 (Pronation/Supination Splint).
Smith & Nephew Inc/Rehabilitation Division 1998 Catalog p. 90 (Pronation/Supination Splint).
Joint Active Systems Brochure.

* cited by examiner

Primary Examiner—Kim M. Lewis
(74) Attorney, Agent, or Firm—Calvo Tervo

(57) ABSTRACT

An orthosis (10) for supination-pronation of the human wrist (92) generally comprises arm cuff (20) secured to arm (80) including forearm platform (26) on forearm (87) directly adjacent elbow (84), a wrist connector (30) including swing arm (33) having a wrist end (36) and an upper end (34) pivotally connected to forearm platform (26) near elbow (84) and about a pivot axis radial to the longitudinal axis of forearm (87), and a wrist cuff (50) adapted to be secured adjacent wrist (92) including a wrist pivot (56) connected to wrist end (36) of swing arm (33). A swinging mechanism (70) applies a force between arm cuff (20) and wrist connector (30) for pivoting swing arm (33) and thereby rotating wrist (92). The length of swing arm (33) is selectably adjustable. Wrist end (36) can be rotated about the longitudinal axis of swing arm (33). Swing arm (33) is attached to wrist connector (55) at selected radial distances from the wrist pivot axis and at selected radial distances from wrist cuff (50).

20 Claims, 2 Drawing Sheets

FIG. 3
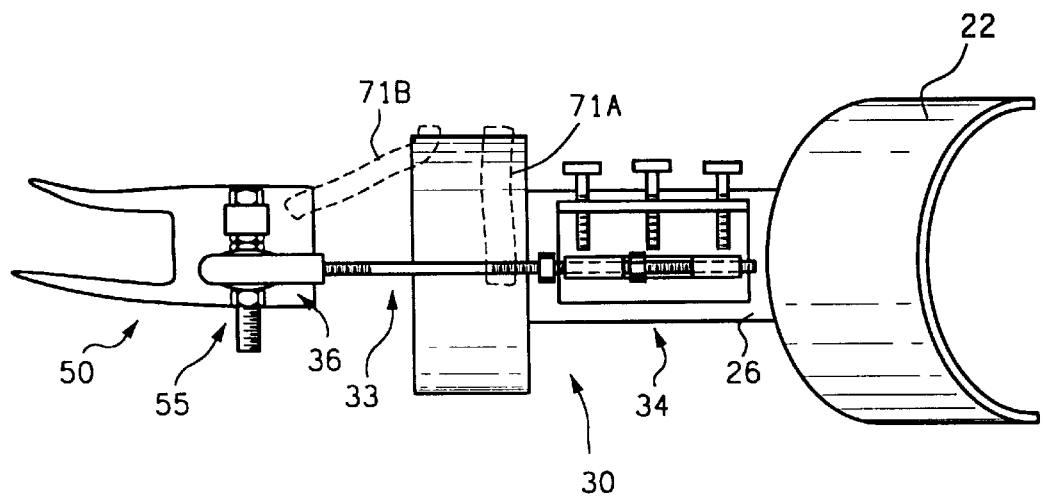
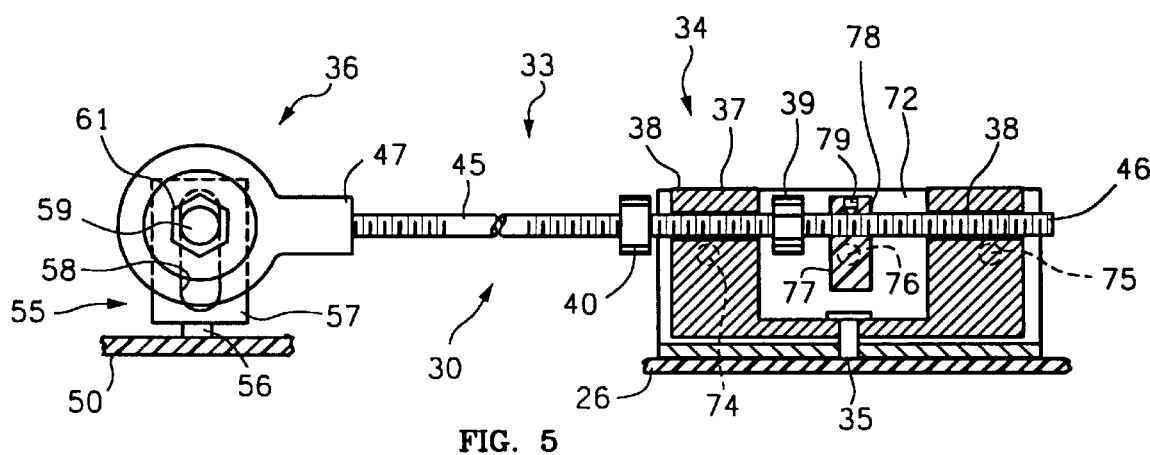
FIG. 4
FIG. 5

ORTHOSIS FOR SUPINATION AND PRONATION OF THE WRIST

FIELD OF THE INVENTION

This invention relates to orthotic devices for rehabilitation of the human wrist and more specifically to an orthosis applying a static, progressive, or dynamic force to pronate or supinate the wrist or to limit the range of motion of pronation or supination.

BACKGROUND OF THE INVENTION

Various devices have been proposed for rotating the human wrist about the longitudinal axis of the forearm. Many of these devices are bulky and complicated. Some of these devices are disposed along the underside of the arm such that the patient cannot lay his arm on a desk or table in a natural manner. Some devices only move the wrist in conjunction with flexure of the elbow. Some devices rotate the wrist through only a small arc, typically 90° or less. Many of these devices must be specifically fabricated for each patient.

Therefore there has been a need for an orthosis for pronation and supination of the human wrist that is simple in construction, that is easily adaptable to a variety of patients, that may be positioned on the top of the forearm such that the arm can be placed naturally on a desk, that is capable of moving the wrist from supine to prone, and that is easily adjustable by the patient to produce the desired results.

SUMMARY OF THE INVENTION

This invention is an orthosis for supination-pronation of the human wrist and it includes an arm cuff secured to the arm including a forearm platform on the forearm directly adjacent the elbow. A wrist connector includes a swing arm having a longitudinal axis and including a wrist end and an upper end pivotally connected to the forearm platform near the elbow and about a pivot axis radial to the longitudinal axis of the forearm. A wrist cuff, adapted to be secured to the arm adjacent the wrist, includes means connected to the wrist end of the swing arm. Swing means interacts between the arm cuff and the wrist connector for applying to the wrist connector a force tending to swing the swing arm about the pivot axis of the upper pivot and thereby rotate the wrist.

The length of the swing arm between the pivot axis of the upper pivot and the wrist end is adjustable and, preferably, is freely variable between selected margins during rotation of the wrist.

The swing means may be a tension member, such as an elastic cord, connected between the wrist connector and the arm cuff. Alternate swing means includes screws interacting between the forearm platform and the swing arm.

Means is provided for selectively rotating the wrist end of the swing arm about the longitudinal axis of the swing arm.

Preferably, a wrist pivot includes a pivot pivotally connecting the wrist end of the swing arm to the wrist cuff about a wrist pivot axis radial to the longitudinal axis of the forearm, a shaft for attaching the wrist end of the swing arm at selected radial distances from the wrist pivot axis, and a radial slot for attaching the wrist end of the swing arm at selected radial distances from the wrist cuff.

Other features and many attendant advantages of the invention will become more apparent upon a reading of the following detailed description together with the drawings in which like reference numerals refer to like parts throughout.

BRIEF DESCRIPTION OF THE DRAWINGS

FIG. 3 is a top plan view of the orthosis of FIG. 1 showing.

FIG. 4 is an enlarged top plan view of the swing arm mechanism of FIG. 1.

FIG. 5 is a right side elevation view of the swing arm mechanism taken on line 5—5 of FIG. 4.

DETAILED DESCRIPTION OF THE PREFERRED EMBODIMENT

Figure 1:
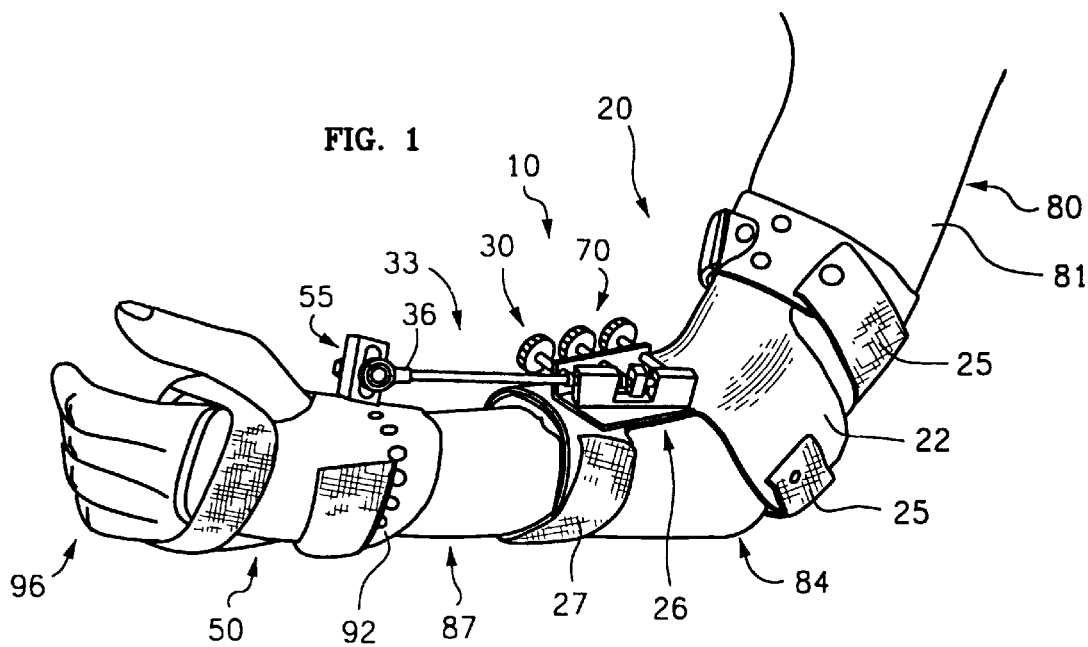
FIG. 1 is a perspective view of a preferred embodiment of the orthosis of the invention in use on a human arm.
Figure 2:
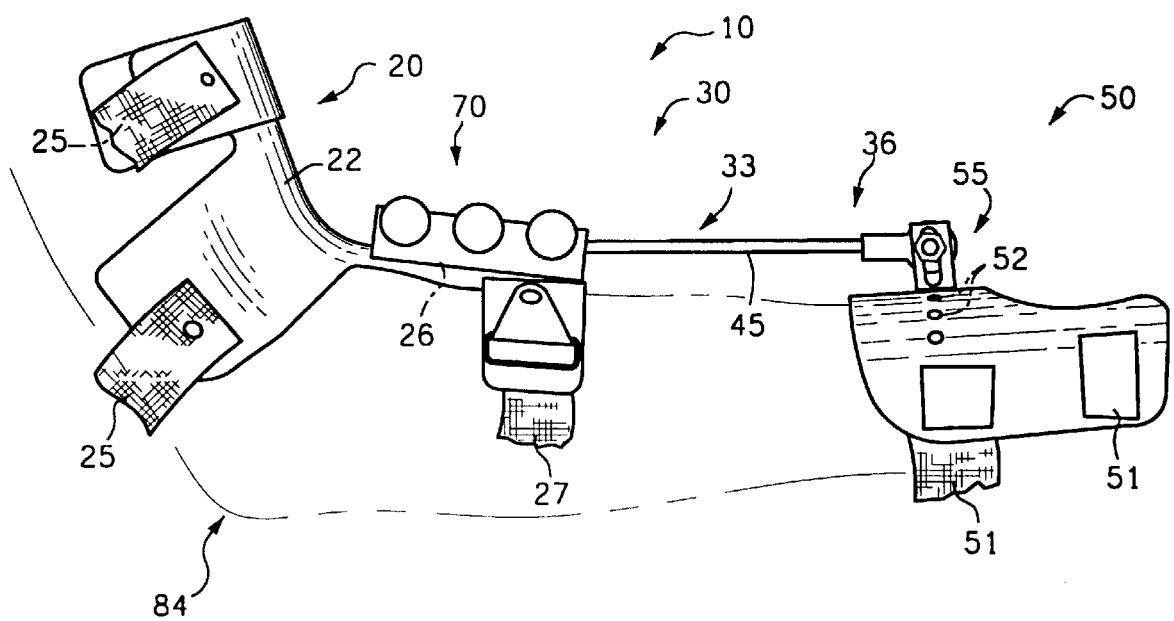
FIG. 2 is a left side elevation view of the orthosis of FIG. 1.

With reference now to the drawings, and more particularly to FIGS. 1 and 2 thereof, FIG. 1 is a perspective view of a preferred embodiment of the orthosis 10 of the invention in use on the left arm 80 of a patient, and FIG. 2 is a left side elevation view of the orthosis 10 of FIG. 1. Arm 80 includes an upper arm 81, a forearm 87, an elbow 84 at their juncture, and hand 96. Forearm 87 has an upper end beginning at elbow 84 and a lower end terminating at wrist 92 and a longitudinal axis therebetween.

Orthosis 10, for supination-pronation of wrist 92, generally comprises a forearm platform 26 secured by arm cuff 20 to arm 80, a wrist connector 30 including a swing arm 33 and a wrist cuff 50, and swing means 70 interacting between forearm platform 26 and wrist connector 30 for applying to wrist connector 30 a force tending to move swing arm 33 through an arc and thereby rotate wrist 92.

Arm cuff 20 includes an upper arm or humeral cuff 22 adapted to be secured to the front of upper arm 81 adjacent elbow 84 and a forearm platform 26 connected to humeral cuff 22 so as to overlie the medial forearm 87 directly adjacent elbow 84. Humeral cuff 22 may be made of any suitable material of types well-known in the art, such as thermoform plastic, and may include means, such as belts or straps 25, to attach it to upper arm 81. Arm Cuff 20 may be made of deformable metal, such as soft aluminum and be formed by the patient or health care professional to fit the patient's arm.

Forearm platform 26 may be made of material similar to humeral cuff 22. Forearm platform 26 may be integrally connected to humeral cuff 22, as shown, or may be hingedly connected, such as around elbow joint by elements well-known in the art, such that platform 26 remains in place lying over forearm 87 during flexing of elbow 84. Forearm platform 26 includes attachment or stabilizing means, such as belts or straps 27, for maintaining or for aiding in maintaining platform 26 in position on forearm during use. Platform 26 could be directly attached, such as by one or more straps 27 to forearm 87 with no need for humeral cuff 22. However, it is desirable that the forearm 87 be as free as possible to rotate about it's longitudinal axis, and the use of humeral cuff 22 holds platform 26 sufficiently in position such that straps 27 may be quite loose or may not be needed at all.

Including now, FIGS. 3–5; FIG. 3 is a top plan view of orthosis 10 of FIG. 1; FIG. 4 is an enlarged top plan view of the wrist connector 30 and swing means 70 of FIG. 3; and FIG. 5 is a right side elevation view of wrist connector 30 and swing means 70 taken on line 5—5 of FIG. 4.

Wrist cuff 50 is adapted to be secured by suitable means, such as by straps 51, to arm 80 adjacent wrist 92. Cuff 50 receives wrist 92 and may, as shown, extend to over the palmar arch. Cuff 50 is firmly attached to the area of wrist 92 so as to transmit received rotational forces to rotation of wrist 92. Wrist cuff 50 includes connecting means 55 connected to swing arm 33.

Cuffs 20,50 may be made by conventional manners well-known in the art. They may be cast of plastic or thermo-formed or made of formed metal. The inner-side of cuffs 20,50 may include conventional padding or an inflatable air bladder to assure a snug and comfortable fit.

Wrist connector 30 generally includes a swing arm 33 and a wrist cuff 50. Swing arm 33 includes a wrist end 36 and an upper end 34 defining a longitudinal axis therebetween. Upper end 34 is pivotally connected, such as by upper pivot 35, to forearm platform 26 near elbow 84. Upper pivot 35 has a pivot axis radial to the longitudinal axis of forearm 87.

Swing arm 33 includes means for adjusting the length of swing arm 33 between the pivot axis of said upper pivot 35 and wrist end 36 and includes length margin means selectively adjustable for allowing the length of swing arm 33 between the pivot axis of upper pivot 35 and wrist end to vary between a selected minimum and selected maximum. Varying the length allows for more accurate fit and the length should vary during some rotations to conform with natural movement of wrist 92.

These length option means are accomplished by the following elements. Swing arm 33 further includes rotation means for rotation of wrist cuff 50 about the longitudinal axis of swing arm 33. The rotation means includes a pivot block 37 pivotally connected by pivot 35 to platform 26 and an elongate rod 45. Block 37 includes through bores 38 for receiving rod 45 which is freely longitudinally slidable therein. Rod 45 has an upper end 46 and a lower end 47. Means, such as adjustable nut 39, engages rod 45, such as by a threaded portion, on the upper side of a bore 38 to selectively define a maximum length of swing arm 33 between the pivot axis of said upper pivot 35 and wrist end 36. Means, such as adjustable nut 40, engages rod 45, such as by a threaded portion, on the lower side of a bore 38 to selectively define a minimum length of swing arm 33 between the pivot axis of said upper pivot 35 and wrist end 36. Of course, both nuts 39,40 can be adjusted against block 37 so as to define a fixed length of rod 45.

Swing means 70 interacts between forearm platform 26 and wrist connector 30 for applying to wrist connector 30 a force tending to swing arm 33 about the pivot axis of upper pivot 35. In alternate embodiments as shown FIG. 3, swing means 70 may include a flexible tension member, such as cord 71A, shown in phantom, connected between wrist connector 30, such as between swing arm 33 and forearm platform 26 or such as cord 71B, shown in phantom, connected to wrist cuff 50. If cords 71A, 71B are non-elastic, then the force to the wrist 92 is static or progressive in nature. If cords 71A,71B are elastic, then the applied force is dynamic in nature.

In the preferred embodiment shown, swing means 70 includes screw means interacting between platform 26 and swing arm 33. Screw means includes bracket 72 attached to platform 26 by any suitable means, such as bonding or rivets, and having threaded bores for receiving adjustment screws, such as first adjustment screw 74 for applying to swing arm 33, such as to block 37, a force tending to pivot swing arm 33 in a first direction about the pivot axis of upper pivot 35 and second adjustment screw 75 for applying to swing arm 33, such as to block 37, a force tending to pivot swing arm 33 in the opposite direction. Alteratively, if screws 74,75 are left, as shown in FIG. 4, not both touching swing arm 33, then they perform as adjustable stop means by allowing pivoting of swing arm 33 to a selected angle in each direction. Thus, screws 74, 75 can apply a static or progressive force for rotation of wrist 92 or may be used to limit the range of rotation of wrist 92 during healing.

Although, straps 71A,71B and screws 74,75 have been shown and described to perform the function of swing means 70, these are just a few of the many contemplated methods. For example, a single worm screw interacting with a radiused gear on the swing arm could be used as could any number of torque applying devices.

Rod 45 is freely journaled in bores 38 in pivot block 37 such that wrist end 36 of swing arm 33 may rotate about the longitudinal axis of swing arm 33.

A selective rotation means selectably rotates wrist end 36 of swing arm 33 a selected angle about the longitudinal axis of swing arm 33. Selective rotation means includes lever arm 77 including bore 78 for freely slidably receiving rod 45 and a set screw 79 for selectively fixing lever arm 77 to rod 45 at a selected location and angle. Adjustable screw 76, threaded through a bore in bracket 72, may be adjusted to encounter and exert a force on lever arm 77 so as to rotate rod 45 a selected angle about the longitudinal axis of swing arm 33. Wrist end 36 is selectably made freely rotational about the longitudinal axis of swing arm 33 by loosening set screw 79.

Wrist connecting means 55 preferably includes wrist pivot means, such as pivot 56, pivotally connecting wrist end 36 of swing arm 33 to wrist cuff 50 about a wrist pivot axis radial to the longitudinal axis of forearm 87. Wrist cuff 50 includes means, such as a plurality of bores 502, for selective attachment of wrist pivot 56 at a plurality of locations. Bores 52 can be used to fine tune or to expand the rotational range of orthosis 10. Means for attaching wrist end 36 of swing arm 33 at selected radial distances from wrist cuff 50 includes pivot block 57 extending radially outward from pivot 56 and having a radial extending slot 58 therethrough in which a threaded shaft 59, preferably disposed orthogonal to wrist pivot axis, is selectively held in a selected radial position by a pair of lock nuts 60. Wrist end 36 is attached to threaded shaft 59, such as by spherical bearing 66 such that swing arm 30 is freely journaled on shaft 59 and also has some angular play. Wrist end 36 of swing arm 33 is attached at selected radial distances from the wrist pivot axis by moving lock nuts 61 along shaft 59. These fittings allow for better fit during all ranges of motion. They also allow for fit if there is radial or ulnar deviation at wrist 92.

Having described the invention, it can be seen that it provides a very convenient device for applying a force to pronate or supinate the wrist or to limit the range of motion of pronation or supination. The force can be static, progressive, or dynamic in nature. Orthosis 10 is easily donned as the rotational force is applied only after orthosis 10 is secured on the patient.

Although a particular embodiment of the invention has been illustrated and described, various changes may be made in the form, composition, construction, and arrangement of the parts without sacrificing any of its advantages. Therefore, it is to be understood that all matter herein is to be interpreted as illustrative and not in any limiting sense, and it is intended to cover in the appended claims such modifications as come within the true spirit and scope of the invention.

I claim:

1. For a patient having an arm including an upper arm, an elbow, and a forearm having a wrist and a longitudinal axis between elbow and wrist; an orthosis for supination-pronation of the wrist; said orthosis comprising:

an arm cuff adapted to be secured to the arm including:
a forearm platform adapted to overlie the inside of the forearm directly adjacent the elbow;

a wrist connector including:
a swing arm having a longitudinal axis and including:
an upper end including:
an upper pivot pivotally connecting said swing arm to said forearm platform and about a pivot axis radial to the longitudinal axis of the forearm during use; and
a wrist end;
a wrist cuff adapted to be secured to the arm adjacent the wrist; said wrist cuff including:
connecting means connecting said wrist end of said swing arm to said wrist cuff near the medial side of the wrist; and
rotation means for rotation of said wrist cuff about the longitudinal axis of said swing arm; and swing means interacting between said arm cuff and said wrist connector for applying to said wrist connector a force tending to swing said swing arm about the pivot axis of said upper pivot.

2. The orthosis of claim 1 wherein said swing arm includes:
means for adjusting the length of said swing arm between the pivot axis of said upper pivot and said wrist end.

3. The orthosis of claim 1 wherein said swing arm includes:
length margin means selectively adjustable for allowing the length of said swing arm between the pivot axis of said upper pivot and said wrist end to freely vary between a selected minimum and selected maximum.

4. The orthosis of claim 1 wherein said swing means includes:
a tension member connected between said wrist connector and said forearm platform.

5. The orthosis of claim 4 wherein said tension member is connected to said wrist cuff.

6. The orthosis of claim 4 wherein said tension member is connected to said swing arm.

7. The orthosis of claim 1 further including:
first adjustable stop means connected to said forearm platform for preventing pivoting of said swing arm about the pivot axis of said upper pivot past a selected angle in a first direction.

8. The orthosis of claim 7 further including:
second adjustable stop means connected to said arm cuff for preventing pivoting of said swing arm about the pivot axis of said upper pivot past a selected angle in a direction opposite the first direction.

9. The orthosis of claim 1 further including:
selective rotation means for selectively rotating said wrist end of said swing arm about the longitudinal axis of said swing arm.

10. For a patient having an arm including an upper arm, an elbow, and a forearm having a wrist and a longitudinal axis between elbow and wrist; an orthosis for supination-pronation of the wrist; said orthosis comprising:

a forearm platform adapted to be secured to the arm so as to adapted to overlie the inside of the forearm directly adjacent the elbow;

a swing arm having a longitudinal axis and including:
an upper end including:
an upper pivot pivotally connecting said swing arm to said forearm platform and about a pivot axis radial to the longitudinal axis of the forearm during use; and
a wrist end;
a wrist cuff adapted to be secured to the arm adjacent the wrist; said wrist cuff including:
connecting means connecting said wrist end of said swing arm to said wrist cuff near the medial side of the wrist; and
rotation means for rotation of said wrist cuff about the longitudinal axis of said swing arm; and swing means interacting between said forearm platform and said swing arm for applying to said swing arm a force tending to swing said swing arm about the pivot axis of said upper pivot.

11. The orthosis of claim 10 wherein said swing means includes:
screw means interacting between said forearm platform and said swing arm for applying to said swing arm a force tending to pivot said swing arm about the pivot axis of said upper pivot.

12. The orthosis of claim 10 wherein said swing means includes:
first screw means interacting between said forearm platform and said swing arm for applying to said swing arm a force tending to pivot said swing arm in a first direction about the pivot axis of said upper pivot; and
second screw means interacting between said cuff and said swing arm for applying to said swing arm a force tending to pivot said swing arm opposite the first direction about the pivot axis of said upper pivot.

13. The orthosis of claim 10 wherein said swing arm includes:
means for adjusting the length of said swing arm between the pivot axis of said upper pivot and said wrist end.

14. The orthosis of claim 10 wherein said swing arm includes:
length margin means selectively adjustable for allowing the length of said swing arm between the pivot axis of said upper pivot and said wrist end to vary between a selected minimum and selected maximum.

15. The orthosis of claim 10 further including:
first adjustable stop means connected to said forearm platform for preventing pivoting of said swing arm about the pivot axis of said upper pivot past a selected angle in a first direction.

16. The orthosis of claim 15 further including:
second adjustable stop means connected to said forearm platform for preventing pivoting of said swing arm about the pivot axis of said upper pivot past a selected angle in a direction opposite the first direction.

17. The orthosis of claim 10 further including:
selective rotation means for selectably rotating said wrist end of said swing arm a selected angle about the longitudinal axis of said swing arm.

18. For a patient having an arm including an upper arm, an elbow, and a forearm having a wrist and a longitudinal axis between elbow and wrist; an orthosis for supination-pronation of the wrist; said orthosis comprising:

a forearm platform adapted to be secured to the arm so as to overlie the inside of the forearm directly adjacent the elbow;

a wrist connector including:
a swing arm having a longitudinal axis and including:

an upper end pivotally connected to said forearm platform near the elbow and about a pivot axis radial to the longitudinal axis of the forearm during use; and a wrist end rotatable about the longitudinal axis of said swing arm; and a wrist cuff adapted to be secured to the arm adjacent the wrist; said wrist cuff including:

connecting means connected to said wrist end of said swing arm including:

wrist pivot means pivotally connecting said wrist end of said swing arm to said wrist cuff about a wrist pivot axis radial to the longitudinal axis of the forearm; said wrist pivot means including:

means for attaching said wrist end of said swing arm at selected radial distances from the wrist pivot axis;

rotation means for rotation of said wrist cuff about the longitudinal axis of said swing arm; and swing means interacting between said forearm platform and said wrist connector for applying to said wrist connector a force tending to swing said swing arm about the pivot axis of said upper pivot.

19. For a patient having an arm including an upper arm, an elbow, and a forearm having a wrist and a longitudinal axis between elbow and wrist; an orthosis for supination-pronation of the wrist; said orthosis comprising:

a forearm platform adapted to be secured to the arm so as to overlie the forearm directly adjacent the elbow;

a wrist connector including:

a swing arm having a longitudinal axis and including:

an upper end pivotally connected to said forearm platform near the elbow and about a pivot axis radial to the longitudinal axis of the forearm during use; and a wrist end rotatable about the longitudinal axis of said swing arm; and a wrist cuff adapted to be secured to the arm adjacent the wrist; said wrist cuff including:

connecting means connected to said wrist end of said swing arm including:

wrist pivot means pivotally connecting said wrist end of said swing arm to said wrist cuff about a wrist pivot axis radial to the longitudinal axis of the forearm; said wrist pivot means including:

means for attaching said wrist end of said swing arm at selected radial distances from said wrist cuff;

rotation means for rotation of said wrist cuff about the longitudinal axis of said swing arm; and swing means interacting between said forearm platform and said wrist connector for applying to said wrist connector a force tending to swing said swing arm about the pivot axis of said upper pivot.

20. For a patient having an arm including an upper arm, an elbow, and a forearm having a wrist and a longitudinal axis between elbow and wrist; an orthosis for supination-pronation of the wrist; said orthosis comprising:

a forearm platform adapted to be secured to the arm so as to overlie the forearm directly adjacent the elbow;

a wrist connector including:

a swing arm having a longitudinal axis and including:

an upper end pivotally connected to said forearm platform near the elbow and about a pivot axis radial to the longitudinal axis of the forearm during use; and a wrist end rotatable about the longitudinal axis of said swing arm; and a wrist cuff adapted to be secured to the arm adjacent the wrist; said wrist cuff including:

connecting means connected to said wrist end of said swing arm including:

wrist pivot means pivotally connecting said wrist end of said swing arm to said wrist cuff about a wrist pivot axis radial to the longitudinal axis of the forearm; said wrist pivot means including:

means for attaching said wrist end of said swing arm such that said wrist end of said swing arm may rotate in a plane orthogonal to an axis orthogonal to the wrist pivot axis;

rotation means for rotation of said wrist cuff about the longitudinal axis of said swing arm; and swing means interacting between said forearm platform and said wrist connector for applying to said wrist connector a force tending to swing said swing arm about the pivot axis of said upper pivot.

* * * * *